US011033879B2

(12) United States Patent
Cheng et al.

(10) Patent No.: US 11,033,879 B2
(45) Date of Patent: *Jun. 15, 2021

(54) BINDERLESS ZEOLITIC ADSORBENTS

(71) Applicant: UOP LLC, Des Plaines, IL (US)

(72) Inventors: Linda S. Cheng, Highland Park, IL (US); David A. Lesch, Hoffman Estates, IL (US)

(73) Assignee: UOP LLC, Des Plaines, IL (US)

(*) Notice: Subject to any disclaimer, the term of this patent is extended or adjusted under 35 U.S.C. 154(b) by 356 days.

This patent is subject to a terminal disclaimer.

(21) Appl. No.: 15/997,600

(22) Filed: Jun. 4, 2018

(65) Prior Publication Data

US 2018/0280926 A1    Oct. 4, 2018

Related U.S. Application Data

(63) Continuation of application No. PCT/US2016/047477, filed on Aug. 18, 2016.

(60) Provisional application No. 62/272,531, filed on Dec. 29, 2015.

(51) Int. Cl.

| | | |
|---|---|---|
| B01J 20/18 | (2006.01) | |
| C01B 39/22 | (2006.01) | |
| C01B 39/20 | (2006.01) | |
| B01J 20/30 | (2006.01) | |
| C07C 7/13 | (2006.01) | |

(52) U.S. Cl.
CPC ........... B01J 20/186 (2013.01); B01J 20/183 (2013.01); B01J 20/3028 (2013.01); B01J 20/3042 (2013.01); B01J 20/3064 (2013.01); B01J 20/3078 (2013.01); B01J 20/3085 (2013.01); C01B 39/20 (2013.01); C01B 39/22 (2013.01); C07C 7/13 (2013.01)

(58) Field of Classification Search
CPC ...... B01J 20/18; B01J 20/186; B01J 20/3028; B01J 20/3042; B01J 20/3078; B01J 20/3085; C01B 39/20; C01B 39/24; C07C 7/13
USPC .......................................................... 502/79
See application file for complete search history.

(56) References Cited

U.S. PATENT DOCUMENTS

| | | | |
|---|---|---|---|
| 2,882,244 | A | 4/1959 | Milton |
| 8,283,274 | B2 | 10/2012 | Cheng et al. |
| 8,530,367 | B2 | 9/2013 | Bouvier et al. |
| 8,557,028 | B2 | 10/2013 | Hurst et al. |
| 8,859,448 | B2 | 10/2014 | Cheng et al. |
| 2009/0326309 | A1 | 12/2009 | Priegnitz et al. |
| 2009/0326310 | A1 | 12/2009 | Kulprathipanja et al. |
| 2012/0264993 | A1 | 10/2012 | Hurst et al. |
| 2015/0306565 | A1 | 10/2015 | Bouvier et al. |
| 2018/0280925 | A1* | 10/2018 | Cheng ................. B01J 20/3042 |

FOREIGN PATENT DOCUMENTS

| | | |
|---|---|---|
| CN | 101495225 A | 7/2009 |
| CN | 102076824 A | 5/2011 |
| CN | 102167652 A | 8/2011 |
| EP | 2527296 A2 | 11/2012 |
| JP | H10101326 A | 4/1998 |
| JP | 2000210557 A | 8/2000 |
| JP | 2002003215 A | 1/2002 |
| JP | 201005542 A | 1/2010 |
| JP | 2010137174 A | 6/2010 |
| JP | 2012533427 A | 12/2012 |
| JP | 201416305 A | 7/2014 |
| RU | 2404122 C1 | 11/2010 |
| RU | 2456238 C1 | 5/2012 |
| RU | 2010145415 A | 5/2012 |
| TW | 201244816 A | 11/2012 |
| TW | 201427768 A | 7/2014 |
| WO | 2010033277 A1 | 3/2010 |
| WO | 2014128125 A1 | 8/2014 |
| WO | 2015028741 A1 | 3/2015 |

OTHER PUBLICATIONS

International Search Report and Written Opinion from corresponding PCT Application No. PCT/US2016/047477, dated Nov. 10, 2016.
International Search Report and Written Opinion from corresponding PCT Application No. PCT/US2016/047469, dated Nov. 10, 2016.
Extended European Search report for European patent application No. EP 16 88 2220, dated Jul. 17, 2019.
Extended European Search report for European patent application No. EP 16 88 2221, dated Jul. 15, 2019.
Seko, Maomi et al., Economical p-Xylene and Ethylbenzene Separated from Mixed Xylene, Ind. Eng. Chem. Prod. Res. Dev., vol. 18, No. 4, 1979.

* cited by examiner

*Primary Examiner* — Edward M Johnson

(57) ABSTRACT

FAU type binderless zeolitic adsorbents and methods for making the FAU type binderless adsorbents are described. The binderless zeolitic adsorbent comprises a first FAU type zeolite having a silica to alumina molar ratio below 3.0; a binder-converted FAU type zeolite having a silica to alumina molar ratio of from about 2.5 to about 6.0, wherein the binder-converted FAU type zeolite may be 5-50% of the binderless zeolitic adsorbent; and cationic exchangeable sites within the binderless zeolitic adsorbent. The FAU type binderless adsorbents may be used for xylene separation and purification in selective adsorptive separation processes using binderless zeolitic adsorbents.

7 Claims, No Drawings

BINDERLESS ZEOLITIC ADSORBENTS

CROSS-REFERENCE TO RELATED APPLICATIONS

This application is a Continuation of copending International Application No. PCT/US2016/047477 filed Aug. 18, 2016, which application claims priority from U.S. Provisional Application No. 62/272,531 filed Dec. 29, 2015, the contents of which cited applications are hereby incorporated by reference in their entirety.

FIELD

The present invention generally relates to binderless zeolitic adsorbents and methods for making the binderless adsorbents. More particularly, the invention relates to FAU type binderless zeolitic adsorbents and methods for making the FAU type binderless adsorbents. The FAU type binderless adsorbents may be used for xylene separation and purification in selective adsorptive separation processes using binderless zeolitic adsorbents.

BACKGROUND

The simulated moving bed (SMB) adsorption process is used commercially in a number of large scale petrochemical separations to recover high purity para-xylene from mixed xylenes. As used herein, "mixed xylenes" refers to a mixture of $C_8$ aromatic isomers that includes ethyl benzene, para-xylene, meta-xylene, and ortho-xylene. High purity para-xylene is used for the production of polyester fibers, resins and films. Para-xylene typically is converted to terephthalic acid or dimethyl terephthalate, which is then reacted with ethylene glycol to form polyethylene terephthalate, the raw material for most polyesters.

The general technique employed in the performance of simulated moving bed adsorptive separation processes is widely described and practiced. Generally, the process simulates a moving bed of adsorbent with continuous counter-current flow of a liquid feed over the adsorbent. Feed and products enter and leave adsorbent beds continuously, at nearly constant compositions. Separation is accomplished by exploiting the differences in affinity of the adsorbent for para-xylene relative to the other $C_8$ aromatic isomers.

Typical adsorbents used in simulated moving bed adsorption processes generally include crystalline aluminosilicate zeolites and can comprise both the natural and synthetic aluminosilicates. Suitable crystalline aluminosilicate zeolites for use as an adsorbent selective for para-xylene include those having aluminosilicate cage structures in which alumina and silica tetrahedra are intimately connected with each other in an open three dimensional crystalline network. The tetrahedra are cross linked by the sharing of oxygen atoms, with spaces between the tetrahedra occupied by water molecules prior to partial or total dehydration of the zeolite. The dehydration results in crystals interlaced with channels having molecular dimensions. In a hydrated form the crystalline aluminosilicate zeolites are generally represented by the formula:

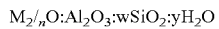

$$M_{2/n}O:Al_2O_3:wSiO_2:yH_2O$$

where "M" is a cation that balances the electrovalence of the tetrahedra and is generally referred to as an exchangeable cationic site, "n" represents the valence of the cation, "w" represents the moles of $SiO_2$, and "y" represents the moles of water. Such crystalline aluminosilicate zeolites that find use as an adsorbent possess relatively well-defined pore structures. The exact type aluminosilicate zeolite is generally identified by the particular silica:alumina molar ratio and the pore dimensions of the cage structures.

Cations (M) occupying exchangeable cationic sites in the zeolitic adsorbent may be replaced with other cations by ion exchange methods well known to those having ordinary skill in the field of crystalline aluminosilicates. Crystalline aluminosilicates, such as Zeolite X with cations at the exchangeable cationic sites within the zeolite, are known to selectively adsorb para-xylene in a mixture comprising at least one other $C_8$ aromatic isomer.

Generally, zeolitic adsorbents used in separative processes contain the zeolitic crystalline material dispersed in an amorphous material or inorganic matrix, having channels and cavities therein which enable liquid access to the crystalline material. Silica, alumina or certain clays and mixtures thereof are typical of such inorganic matrix materials, which act as a "binder" to form or agglomerate the zeolitic crystalline particles that otherwise would comprise a fine powder. Agglomerated zeolitic adsorbents may thus be in the form of particles such as extrudates, aggregates, tablets, macrospheres such as beads, granules, or the like.

The binder is typically inert and does not contribute to any selective adsorption. Efforts have been made to improve adsorbent productivity by increasing the selective part (zeolite volume) within adsorbents by converting the binder into selective zeolite in a conversion process referred to as "zeolitization", while maintaining the strength and macroporosity of the zeolitic adsorbent. This conversion process results in a "binderless" zeolitic adsorbent. While this conversion process has resulted in an increase in adsorbent productivity, still further increases in process performance and decreases in operating costs for adsorptive separation processes are sought.

Accordingly, it is desirable to provide a binderless zeolitic adsorbent that decreases the amount of adsorbent and desorbent required to process a fixed amount of feed. It is also desirable to provide a method for forming such a binderless adsorbent. Furthermore, other desirable features and characteristics of the present invention will become apparent from the subsequent detailed description of the invention and the appended claims, taken in conjunction with the accompanying background of the invention.

SUMMARY

The present invention provides a binderless zeolitic adsorbent and a method for producing the binderless zeolitic adsorbent.

A first embodiment of the invention is a binderless zeolitic adsorbent comprising a first FAU type zeolite having a silica to alumina molar ratio below 3.0; a binder-converted FAU type zeolite having a silica to alumina molar ratio of from about 2.5 to about 6.0, wherein the binder-converted FAU type zeolite may be 5-50% of the binderless zeolitic adsorbent; and cationic exchangeable sites within the binderless zeolitic adsorbent. An embodiment of the invention is one, any or all of prior embodiments in this paragraph up through the first embodiment in this paragraph, wherein the binder-converted FAU zeolite includes a silica to alumina molar ratio of from about 3.0 to about 6.0. An embodiment of the invention is one, any or all of prior embodiments in this paragraph up through the first embodiment in this paragraph, wherein at least 95% of the binderless zeolitic adsorbent is FAU type zeolite. An embodiment of the invention is one, any or all of prior embodiments in this paragraph up through the first embodiment in this paragraph, wherein at least 98% of the binderless zeolitic adsorbent is FAU type zeolite. An embodiment of the invention is one, any or all of prior embodiments in this paragraph up through the first embodiment in this paragraph, wherein the cationic exchangeable sites may be alkali/alkaline earth cations. An embodiment of the invention is one, any or all of prior embodiments in this paragraph up through the first embodiment in this paragraph, wherein the cationic exchangeable sites may be barium, potassium, sodium, or any combination of barium, potassium, or sodium. An embodiment of the invention is one, any or all of prior embodiments in this paragraph up through the first embodiment in this paragraph, wherein the non-zeolitic binder comprises silica, alumina, or a combination of silica and alumina.

A second embodiment of the invention is a method for producing a binderless zeolitic adsorbent comprising forming agglomerates having ion-exchangeable sites, the agglomerates formed from FAU type zeolite having a silica to alumina molar ratio below 3.0, a non-zeolitic binder comprising silica, alumina, or a combination of silica and alumina, and a forming aid, wherein agglomerates are formed from greater than 50% of the FAU type zeolite; applying a thermal treatment to precondition the binder and dissipate the forming aid; applying a hydrothermal treatment with a solution containing at least one source of hydroxide to convert non-zeolitic material into FAU type zeolite material; and drying the binderless zeolitic adsorbent. An embodiment of the invention is one, any or all of prior embodiments in this paragraph up through the second embodiment in this paragraph, wherein at least 95% of the binderless zeolitic adsorbent is FAU type zeolite. An embodiment of the invention is one, any or all of prior embodiments in this paragraph up through the second embodiment in this paragraph, wherein at least 98% of the binderless zeolitic adsorbent is FAU type zeolite. An embodiment of the invention is one, any or all of prior embodiments in this paragraph up through the second embodiment in this paragraph, wherein the solution containing hydroxide further comprises silicon, aluminum, or a mixture of both silicon and aluminum. An embodiment of the invention is one, any or all of prior embodiments in this paragraph up through the second embodiment in this paragraph, further comprising exchanging the ion-exchangeable sites. An embodiment of the invention is one, any or all of prior embodiments in this paragraph up through the second embodiment in this paragraph, wherein drying the binderless zeolitic adsorbent assures that the binderless zeolitic adsorbent contains about 1% to about 7% of water. An embodiment of the invention is one, any or all of prior embodiments in this paragraph up through the second embodiment in this paragraph, wherein forming agglomerates further comprises agglomerates having a particle size in the range of about 0.3 mm to about 0.8 mm. An embodiment of the invention is one, any or all of prior embodiments in this paragraph up through the second embodiment in this paragraph, wherein the step of forming agglomerates comprises combining FAU type zeolite and kaolin clay binder in amounts, respectively, of between about 80 to about 90 weight percent and between about 10 and about 20 weight percent of the agglomerated binderless FAU type zeolite adsorbent, and mixing with cornstarch in an amount of up to about 5% by weight of the combined weight percent of the binder-converted FAU type zeolite and the FAU type zeolite. An embodiment of the invention is one, any or all of prior embodiments in this paragraph up through the second embodiment in this paragraph, wherein the step of activating the agglomerates comprises heating the agglomerates to at least 625° C. and the step of converting the meta-kaolin clay binder into binder-converted zeolite comprises caustic digesting the meta-kaolin clay binder with an aqueous alkali metal hydroxide solution.

Additional objects, advantages and novel features of the examples will be set forth in part in the description which follows, and in part will become apparent to those skilled in the art upon examination of the following description or may be learned by production or operation of the examples. The objects and advantages of the concepts may be realized and attained by means of the methodologies, instrumentalities and combinations particularly pointed out in the appended claims.

Definitions

As used herein, the term "stream" can include various hydrocarbon molecules, such as straight-chain, branched, or cyclic alkanes, alkenes, alkadienes, and alkynes, and optionally other substances, such as gases, e.g., hydrogen, or impurities, such as metals, and sulfur and nitrogen compounds. The stream can also include aromatic and non-aromatic hydrocarbons. Moreover, the hydrocarbon molecules may be abbreviated $C_1$, $C_2$, $C_3$ . . . $C_n$ where "n" represents the number of carbon atoms in the one or more hydrocarbon molecules. Furthermore, a superscript "+" or "−" may be used with an abbreviated one or more hydrocarbons notation, e.g., $C_3^+$ or $C_3^-$, which is inclusive of the abbreviated one or more hydrocarbons. As an example, the abbreviation "$C_3$" means one or more hydrocarbon molecules of three and/or more carbon atoms.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "weight percent" may be abbreviated "wt %".

As used herein, the term "atomic ratio" may be used interchangeably with "mole ratio".

As used herein, the term "FAU type" can refer to faujasite zeolites, such as zeolites X and Y.

DETAILED DESCRIPTION

The following detailed description of the invention is exemplary in nature and is not intended to limit the invention or the application and uses of the invention. Also, there is no intention to be bound by any theory presented in the preceding background of the invention or the following detailed description of the invention.

A first embodiment of the invention is a binderless zeolitic adsorbent comprising a first FAU type zeolite having a silica to alumina molar ratio below 3.0; a binder-converted FAU type zeolite having a silica to alumina molar ratio of from about 2.5 to about 6.0, wherein the binder-converted FAU type zeolite may be 5-50% of the binderless zeolitic adsorbent; and cationic exchangeable sites within the binderless zeolitic adsorbent. An embodiment of the invention is one, any or all of prior embodiments in this paragraph up through the first embodiment in this paragraph, wherein the binder-converted FAU zeolite includes a silica to alumina molar ratio of from about 3.0 to about 6.0. An embodiment of the invention is one, any or all of prior embodiments in this paragraph up through the first embodiment in this paragraph, wherein at least 95% of the binderless zeolitic adsorbent is FAU type zeolite. An embodiment of the invention is one, any or all of prior embodiments in this paragraph up through the first embodiment in this paragraph, wherein at least 98% of the binderless zeolitic adsorbent is FAU type zeolite. An embodiment of the invention is one, any or all of prior embodiments in this paragraph up through the first embodiment in this paragraph, wherein the cationic exchangeable sites may be alkali/alkaline earth cations. An embodiment of the invention is one, any or all of prior embodiments in this paragraph up through the first embodiment in this paragraph, wherein the cationic exchangeable sites may be barium, potassium, sodium, or any combination of barium, potassium, or sodium. An embodiment of the invention is one, any or all of prior embodiments in this paragraph up through the first embodiment in this paragraph, wherein the non-zeolitic binder comprises silica, alumina, or a combination of silica and alumina.

A second embodiment of the invention is a method for producing a binderless zeolitic adsorbent comprising forming agglomerates having ion-exchangeable sites, the agglomerates formed from FAU type zeolite having a silica to alumina molar ratio below 3.0, a non-zeolitic binder comprising silica, alumina, or a combination of silica and alumina, and a forming aid, wherein agglomerates are formed from greater than 50% of the FAU type zeolite; applying a thermal treatment to precondition the binder and dissipate the forming aid; applying a hydrothermal treatment with a solution containing at least one source of hydroxide to convert non-zeolitic material into FAU type zeolite material; and drying the binderless zeolitic adsorbent. An embodiment of the invention is one, any or all of prior embodiments in this paragraph up through the second embodiment in this paragraph, wherein at least 95% of the binderless zeolitic adsorbent is FAU type zeolite. An embodiment of the invention is one, any or all of prior embodiments in this paragraph up through the second embodiment in this paragraph, wherein at least 98% of the binderless zeolitic adsorbent is FAU type zeolite. An embodiment of the invention is one, any or all of prior embodiments in this paragraph up through the second embodiment in this paragraph, wherein the solution containing hydroxide further comprises silicon, aluminum, or a mixture of both silicon and aluminum. An embodiment of the invention is one, any or all of prior embodiments in this paragraph up through the second embodiment in this paragraph, further comprising exchanging the ion-exchangeable sites. An embodiment of the invention is one, any or all of prior embodiments in this paragraph up through the second embodiment in this paragraph, wherein drying the binderless zeolitic adsorbent assures that the binderless zeolitic adsorbent contains about 1% to about 7% of water. An embodiment of the invention is one, any or all of prior embodiments in this paragraph up through the second embodiment in this paragraph, wherein forming agglomerates further comprises agglomerates having a particle size in the range of about 0.3 mm to about 0.8 mm. An embodiment of the invention is one, any or all of prior embodiments in this paragraph up through the second embodiment in this paragraph, wherein the step of forming agglomerates comprises combining FAU type zeolite and kaolin clay binder in amounts, respectively, of between about 80 to about 90 weight percent and between about 10 and about 20 weight percent of the agglomerated binderless FAU type zeolite adsorbent, and mixing with cornstarch in an amount of up to about 5% by weight of the combined weight percent of the binder-converted FAU type zeolite and the FAU type zeolite. An embodiment of the invention is one, any or all of prior embodiments in this paragraph up through the second embodiment in this paragraph, wherein the step of activating the agglomerates comprises heating the agglomerates to at least 625° C. and the step of converting the meta-kaolin clay binder into binder-converted zeolite comprises caustic digesting the meta-kaolin clay binder with an aqueous alkali metal hydroxide solution.

The preferred class of zeolite of the instant invention is faujasite, including both synthetic X and Y types. Most preferred is the X type as disclosed generally in U.S. Pat. No. 2,882,244, incorporated herein by reference. The crystals of Zeolite X are basically three dimensional frameworks of $SiO_4$ and $AlO_4$ tetrahedra crosslinked by sharing of oxygen atoms. The electrovalence of each tetrahedron containing aluminum is balanced by the presence in the aluminosilicate framework of a cation such as an alkali metal ion. The void spaces in the framework are occupied by water molecules.

In one embodiment, the method for preparing the FAU-type zeolite adsorbent begins with the formation of adsorbent agglomerates comprised of the Zeolite X and inert binder. The Zeolite X is agglomerated into adsorbent beads using the inert binder by mixing at ambient temperature with water. In a preferred embodiment, the inert binder comprises kaolin clay with a silica:alumina molar ratio in the range of about 2.0 to about 2.2, preferably about 2.0. Kaolin clay is available from U.S. Silica Co., Berkeley Springs, W. Va., for example. The beads may be comprised of from about 80 to about 90 wt % of Zeolite X and about 10 to about 20 wt % of kaolin clay binder (on a volatile-free basis). The kaolin clay binder holds the starting zeolite powder together to form adsorbent beads with a particle size in the range of about 0.3 mm to about 0.8 mm and having increased mechanical strength as shown by water attrition tests as hereinafter described. While agglomerates in the form of beads have been described, the invention is not so limited. The Zeolite X may be agglomerated into other forms of particles such as extrudates, aggregates, tablets, macrospheres, granules, or the like.

In an exemplary embodiment, additives, such as cornstarch, may also be mixed with the Zeolite X and inert binder during the agglomerate-forming step. Cornstarch may be added in an amount from about 0 to about 5.0 wt % (on a volatile-free basis) of the total combined weight of the binder-converted zeolite portion and the starting Zeolite X for purposes as hereinafter described. Other additives may include polymers and fibers.

To convert the kaolin clay binder to a binder-converted zeolite, the agglomerates are activated at about 625° C. or higher to convert the kaolin clay binder into meta-kaolin clay binder. The kaolin clay binder undergoes an endothermic dehydroxylation reaction and converts to a disordered meta-kaolin phase. If cornstarch was previously added, it burns off during this step.

Next, the meta-kaolin clay binder is then caustic-digested at a temperature of about 88° C. by a solution containing sodium silicate and sodium hydroxide and the meta-kaolin binder is converted to binder-converted zeolite having a silica: alumina molar ratio in the range of from about 2.5 to about 6.0. The conversion results in an increase in selective pore volume as determined through McBain $O_2$ capacity measurements at liquid $O_2$ temperature. Such measurement is described in ZEOLITE MOLECULAR SIEVES: STRUCTURE, CHEMISTRY AND USE by Donald W. Breck, John Wiley & Sons, 1974. Thus, the adsorbent beads comprise substantially 100% zeolite with negligible inert binder, forming "binderless" zeolitic adsorbent beads. The adsorbent beads comprise a Zeolite X portion (from the starting Zeolite X) with a silica:alumina molar ratio in the range of 2.5±0.5, and the binder-converted zeolite portion with a silica:alumina molar ratio in the range of about 2.5 to about 6.0. While the conversion of a kaolin clay binder to binder-converted zeolite has been described, the invention is not so limited. For example, other clay binders or alumina or silica binders may be converted to a binder-converted zeolite. Non-limiting examples include clays belonging to the halloysite family. In addition, while the use of a sodium hydroxide solution has been described as the caustic solution for binder conversion, the invention is not so limited. In addition to sodium hydroxide, other aqueous alkali metal hydroxide solutions may be used for conversion. Non-limiting examples include a solution of potassium hydroxide or a mixture of sodium hydroxide and potassium hydroxide.

The binderless zeolitic adsorbent beads are then exposed to alkali or alkaline earth cations for ion-exchange to produce the FAU type binderless zeolitic adsorbent.

In one exemplary embodiment, the exchange can be in a single step with a mixture of Ba and K. Alternatively, the exchanges may take place sequentially, with each step exchanging an appropriate amount of ions to produce a FAU type binderless zeolitic adsorbent While the ion exchange is described as occurring after agglomeration of the Zeolite X and after conversion, the invention is not so limited. The exchange with Ba and K may occur prior to agglomeration of the Zeolite X or after forming agglomerates and before conversion, but some ion exchange after conversion may still be required as sodium hydroxide is used to convert the meta-kaolin to zeolite. Cation exchange capacity calculations in Zeolite X are described in "Zeolite Molecular Sieves: Structure, Chemistry, and Use" by Donald W. Breck, John Wiley & Sons, 1974.

Next, the FAU type binderless zeolitic adsorbent is dried to fix its water content. In this regard, the FAU type binderless zeolitic adsorbent is activated by washing and drying the beads to about 1 to about 7% Loss on Ignition (LOI at 900° C.). The drying is generally carried out by thermal activation, preferably at temperatures of from about 175° C. to about 250° Celsius. The water content of the adsorbent is expressed herein in terms of the recognized LOI test at 900° C. The LOI test is described in UOP Test Method No. UOP954-03 (available through ASTM International, 100 Barr Harbor Drive, PO Box C700, West Conshohocken, Pa., 19428-2959 USA).

As noted above, cornstarch may be added to the Zeolite X and the clay binder mixture during the bead-forming stage. The addition of cornstarch increases the meso- and macroporosity of the adsorbent beads, as explained in more detail below. As used herein and conventionally, "macro-pores" are defined as pores having a pore diameter greater than 50 nm and "meso-pores" are defined as pores having a pore diameter between 2 and 50 nm. Macro- and meso-porosity facilitates conversion of the binder by permitting the sodium hydroxide conversion solution to flow throughout the binder. The macro- and meso-pores also help improve the mass transfer rate of the FAU type binderless zeolitic adsorbent.

The binderless adsorbents may be used for xylene separation and purification in selective adsorptive separation processes using binderless zeolitic adsorbents, such as purifying high purity paraxylene or meta-xylene. Non-limiting examples include: batch and continuous operating modes; liquid phase and gas phase operations; fix-bed, moving bed, and simulated moving bed operations; and counter-current and co-current flows. In an exemplary embodiment, the binderless zeolitic adsorbent is used in counter-current, liquid phase, simulating moving bed, adsorptive separation processes for the recovery of para-xylene from mixed xylenes. The adsorbents are selective for para-xylene. The desorbent used for the SMB process may comprise para-diethylbenzene, toluene, benzene, or indane.

EXAMPLES

The following example is intended to further illustrate the subject adsorbent. This illustration of an embodiment of the present disclosure is not meant to limit the claims of this present disclosure to the particular details of these examples. These examples are based on engineering calculations and actual operating experience with similar processes.

85 wt % zeolite X powder and 15 wt % kaolin clay were first extruded as 1/16" cylinders using 3 wt % CMC as extrusion aid. Extrudates were dried in an oven overnight at 100° C. Next, the extrudates were activated using the following steps: 2° C./minute ramp to 300° C. and held for two hours followed with a 5° C./minute ramp to 675° C. and held for three hours, and finally cool down to 100° C. at 10° C./minute. After the extrudates cooled to room temperature they were crushed and sized to 20/40 mesh. 10 g of meshed extrudates were next treated with a solution that was prepared by targeting the following gel molar oxide ratio: $Al_2O_3$:10.45 $SiO_2$:4.5 $Na_2O$:500 $H_2O$ (including the binder composition but not the zeolite X powder). The solution was made up with 11.82 g sodium silicate; 2.09 g 50% NaOH solution; and 52.13 g $H_2O$, and added to a glass flask, covered and brought up to digestion temperature, 88° C. in a hot water bath. Once the solution was at temperature the meshed extrudates were added to the flask, which was again covered and placed back into the water bath. Finally, the water bath was covered, the shaker component started, and the program was set to remain at temperature for 20 hours and programmed to shut off automatically. Once cooled to room temperature, the flask's mother liquor was decanted and the converted solid was washed with deionized water at ambient temperature until the wash water pH was <11. Samples were air-dried overnight at room temperature.

From the foregoing, it is to be appreciated that by converting the binder to zeolite, the gravimetric capacity of the adsorbent increases which allows more feed to be processed with a given mass of adsorbent. Further, by converting a binder which is low in silica content, e.g. kaolin clay or alumina, to a zeolite that has a relatively high silica content, a large increase in volumetric capacity can be realized. This is due to the addition of the mass of silica and charge balancing cations while maintaining a constant volume of the formed adsorbent body. This increase in volumetric capacity allows significantly more feed to be processed with the same volume of adsorbent.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

Specific Embodiments

While the following is described in conjunction with specific embodiments, it will be understood that this description is intended to illustrate and not limit the scope of the preceding description and the appended claims.

A first embodiment of the invention is a binderless zeolitic adsorbent comprising a first FAU type zeolite having a silica to alumina molar ratio below 3.0; a binder-converted FAU type zeolite having a silica to alumina molar ratio of from about 2.5 to about 6.0, wherein the binder-converted FAU type zeolite may be 5-50% of the binderless zeolitic adsorbent; and cationic exchangeable sites within the binderless zeolitic adsorbent. An embodiment of the invention is one, any or all of prior embodiments in this paragraph up through the first embodiment in this paragraph, wherein the binder-converted FAU zeolite includes a silica to alumina molar ratio of from about 3.0 to about 6.0. An embodiment of the invention is one, any or all of prior embodiments in this paragraph up through the first embodiment in this paragraph, wherein at least 95% of the binderless zeolitic adsorbent is FAU type zeolite. An embodiment of the invention is one, any or all of prior embodiments in this paragraph up through the first embodiment in this paragraph, wherein at least 98% of the binderless zeolitic adsorbent is FAU type zeolite. An embodiment of the invention is one, any or all of prior embodiments in this paragraph up through the first embodiment in this paragraph, wherein the cationic exchangeable sites may be alkali/alkaline earth cations. An embodiment of the invention is one, any or all of prior embodiments in this paragraph up through the first embodiment in this paragraph, wherein the cationic exchangeable sites may be barium, potassium, sodium, or any combination of barium, potassium, or sodium. An embodiment of the invention is one, any or all of prior embodiments in this paragraph up through the first embodiment in this paragraph, wherein the non-zeolitic binder comprises silica, alumina, or a combination of silica and alumina.

A second embodiment of the invention is a method for producing a binderless zeolitic adsorbent comprising forming agglomerates having ion-exchangeable sites, the agglomerates formed from FAU type zeolite having a silica to alumina molar ratio below 3.0, a non-zeolitic binder comprising silica, alumina, or a combination of silica and alumina, and a forming aid, wherein agglomerates are formed from greater than 50% of the FAU type zeolite; applying a thermal treatment to precondition the binder and dissipate the forming aid; applying a hydrothermal treatment with a solution containing at least one source of hydroxide to convert non-zeolitic material into FAU type zeolite material; and drying the binderless zeolitic adsorbent. An embodiment of the invention is one, any or all of prior embodiments in this paragraph up through the second embodiment in this paragraph, wherein at least 95% of the binderless zeolitic adsorbent is FAU type zeolite. An embodiment of the invention is one, any or all of prior embodiments in this paragraph up through the second embodiment in this paragraph, wherein at least 98% of the binderless zeolitic adsorbent is FAU type zeolite. An embodiment of the invention is one, any or all of prior embodiments in this paragraph up through the second embodiment in this paragraph, wherein the solution containing hydroxide further comprises silicon, aluminum, or a mixture of both silicon and aluminum. An embodiment of the invention is one, any or all of prior embodiments in this paragraph up through the second embodiment in this paragraph, further comprising exchanging the ion-exchangeable sites. An embodiment of the invention is one, any or all of prior embodiments in this paragraph up through the second embodiment in this paragraph, wherein drying the binderless zeolitic adsorbent assures that the binderless zeolitic adsorbent contains about 1% to about 7% of water. An embodiment of the invention is one, any or all of prior embodiments in this paragraph up through the second embodiment in this paragraph, wherein forming agglomerates further comprises agglomerates having a particle size in the range of about 0.3 mm to about 0.8 mm. An embodiment of the invention is one, any or all of prior embodiments in this paragraph up through the second embodiment in this paragraph, wherein the step of forming agglomerates comprises combining FAU type zeolite and kaolin clay binder in amounts, respectively, of between about 80 to about 90 weight percent and between about 10 and about 20 weight percent of the agglomerated binderless FAU type zeolite adsorbent, and mixing with cornstarch in an amount of up to about 5% by weight of the combined weight percent of the binder-converted FAU type zeolite and the FAU type zeolite. An embodiment of the invention is one, any or all of prior embodiments in this paragraph up through the second embodiment in this paragraph, wherein the step of activating the agglomerates comprises heating the agglomerates to at least 625° C. and the step of converting the meta-kaolin clay binder into binder-converted zeolite comprises caustic digesting the meta-kaolin clay binder with an aqueous alkali metal hydroxide solution.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A binderless zeolitic adsorbent comprising:
a first FAU type zeolite having a silica to alumina molar ratio below 3.0, wherein the first FAU type zeolite is Zeolite X;
a binder-converted FAU type zeolite having a silica to alumina molar ratio of from about 3.0 to about 6.0, wherein the binder-converted FAU type zeolite is Zeolite Y, and wherein the binder-converted FAU type zeolite is 5-50% of the binderless zeolitic adsorbent; and
cationic exchangeable sites within the binderless zeolitic adsorbent.

2. The binderless zeolitic adsorbent of claim 1, wherein at least 95% of the binderless zeolitic adsorbent is FAU type zeolite.

3. The binderless zeolitic adsorbent of claim 1, wherein at least 98% of the binderless zeolitic adsorbent is FAU type zeolite.

4. The binderless zeolitic adsorbent of claim 1, wherein the cationic exchangeable sites may be alkali/alkaline earth cations.

5. The binderless zeolitic adsorbent of claim 1, wherein the cationic exchangeable sites may be barium, potassium, sodium, or any combination of barium, potassium, or sodium.

6. The binderless zeolitic adsorbent of claim 1, wherein the non-zeolitic binder comprises silica, alumina, or a combination of silica and alumina.

7. The binderless zeolitic adsorbent of claim 1, wherein the first FAU type zeolite is about 80 to about 90% of the binderless zeolitic adsorbent, and wherein binder-converted FAU type zeolite is about 10 to about 20% of the binderless zeolitic adsorbent.

* * * * *